United States Patent [19]

Michelson

[11] Patent Number: 4,481,943

[45] Date of Patent: Nov. 13, 1984

[54] ORTHOPEDIC SUPPORT FRAME

[76] Inventor: Gary K. Michelson, 117 38th Pl., Manhattan Beach, Calif. 90266

[21] Appl. No.: 473,710

[22] Filed: Mar. 9, 1983

[51] Int. Cl.³ .............................................. A61F 13/00
[52] U.S. Cl. ..................................... 128/134; 269/328
[58] Field of Search ...................... 128/68, 69, 70, 133, 128/134; 269/322, 328

[56] References Cited

U.S. PATENT DOCUMENTS

| | | | |
|---|---|---|---|
| 2,631,301 | 3/1953 | Hyland | 128/134 X |
| 2,887,151 | 5/1959 | Springer | 128/70 X |
| 3,491,385 | 1/1970 | Werner | 128/68 X |

*Primary Examiner*—John D. Yasko
*Attorney, Agent, or Firm*—Blakely, Sokoloff, Taylor & Zafman

[57] ABSTRACT

The present invention is an orthopedic support frame for use during orthopedic surgery. The frame provides increased stability of the patient during surgery in the modified knee-chest position with better control of flexion and extension. The frame comprises two triangular shaped brackets, each having a first and second frame members disposed at right angles to each other and having a third frame member extending from the end of the first member to the end of the second member. The mounting brackets are disposed in parallel spaced apart relationship with the second frame member comprising mounting means for mounting the frame on an operating table. At least one stationary posterior support member which is rigidly affixed to and across the first frame members and supports the posterior of the patient. A locking member is disposed below the posterior support member and is adjustably affixed to and across the first frame member. A cross member may be affixed to and extend between the third frame members to provide additional structural strength to the frame.

10 Claims, 4 Drawing Figures

ORTHOPEDIC SUPPORT FRAME

BACKGROUND OF THE INVENTION

1. Field of the Invention

This invention relates to support devices to maintain the spine in a suitable position for spinal surgery.

2. Prior Art

During orthopedic surgery, when the lumbar spine is to be operated on, the patient must be placed in a position which takes pressure off the chest cavity and abdomen. Presently, there are three conventional positions in which a patient may be placed during surgery. In the first, or "prone position", the patient is placed face down over bolsters on the operating table. The degree of exposure of the spine is well controlled, however, the abdomen and chest often become depressed. This thoracic (chest) compression often interferes with proper ventilation of the anesthetized patient and increases the resistance to return of venous blood to the heart. Furthermore, the abdominal compression may produce transmitted compression of the inferior vena cava which may cause engorgement of the epidural veins. As a result, the patient will have a tendency to bleed which presents a serious obstacle to the surgeon as landmarks are obscured, operating time prolonged, and vital structures are endangered. Also blood loss may pose a life threatening situation which makes demands on the surgeon and compromises the extent of the proposed surgery.

In the second, or "lateral recumbent position," the patient respirates freely and the venous return is not blocked. However, in this position, spinal fusion to the tips of the transverse processes is difficult.

In the third and position, the "knee-chest position," the lumbar spine is flexed and the interlaminar spaces in the spinal column are opened widely. In this position, the patient's respiration is satisfactory and no pressure is exerted on the inferior vena cava. However, flexing the interlaminar spaces does tend to increase tension on nerve roots which have already been quite tight due to disc herniation. The full flexion of both hips and knees is required and may impede venous return from the legs, produce stasis and causes deep-vein thrombosis. Furthermore, in this position, the patient is often unstable and is prone to motion during surgery. The knee chest position can be improved as to enhance the benfits of the position while decreasing its liabilites. This produces the so called modified knee-chest position where the knees are not actually against the chest but rather bent to a right angle with the hips similarly bent to a right angle. A special frame is required to maintain a patient in this modified knee-chest position.

One such device was developed by Hastings and is disclosed in an article in the *Canadian Journal of Surgery,* pages 251-253, volume 12, April 1969. Hastings discloses a wooden frame having an adjustable seat and a removable cross bar extending across the frame to add stability. The frame is attached to a standard operating table by a standard metal mount which rests on the operating table. The degree of flexion or extension of the lumbar spine is controlled by changing the height of the rest that supports the patient's chest.

A problem encountered in using this particular frame is that the height and location of the frame cannot be adjusted to accommodate patients of various sizes and shapes. For example, if the patient is to be fused in extension, a higher frame must be selected rather than adjusting the height of the frame. Furthermore, since the frame is comprised of wood, it exposes a rough surface that can cause injury to the patient, due to splintering and absorption of blood in the wood material. Also, because the seating platform is adjustable, it has a tendency to slide under the weight of a heavy patient, causing the patient to move out of proper position and thereby making the surgical process more difficult and time consuming.

SUMMARY OF THE INVENTION

The present invention is an orthopedic support frame for use during orthopedic surgery. The frame provides increased stability of the patient during surgery in the modified knee-chest position with better control of flexion and extension. The frame comprises two triangular shaped brackets, each having a first and second frame members disposed at right angles to each other and having a third frame member extending from the end of the first member to the end of the second member. The mounting brackets are disposed in parallel spaced apart relationship with the second frame member comprising mounting means for mounting the frame on an operating table. At least one stationary posterior support member which is rigidly affixed to and across the first frame members and supports the posterior of the patient. A locking member is disposed below the posterior support member and is adjustably affixed to and across the first frame member. A cross member may be affixed to and extend between the third frame members to provide additional structural strength to the frame.

When the frame is in use, the patient's legs are inserted calf side up, between the adjustable locking member and the operating table. The locking member is lowered so that it rests against the back of the patient's knees just below the knee joint. The locking member is then fixedly clamped to the first frame members thereby maintaining the patient in a fixed position during adjustment of the operating table and during surgery.

The mounting means comprise a plurality of mounting rods to which attach the frame to the side rails of the operating table. The vertical position of the frame in relation to the table can be preselected, thereby lowering or increasing the height of the frame as a further adjustment for larger patients.

In operation, once the patient has his legs affixed between the locking member and the operating table, the operating table is rotated to an angle so that the patient gently falls into a sitting position on the posterior stationary support member. The angle of the operating table and of the support frame keeps the patient from falling out of the knee-chest position during surgery.

The frame has been designed to allow placement with the patient already on the operating table and in the prone position though it can also be readily used if plated first.

DETAILED DESCRIPTION OF THE INVENTION

Figure 1:
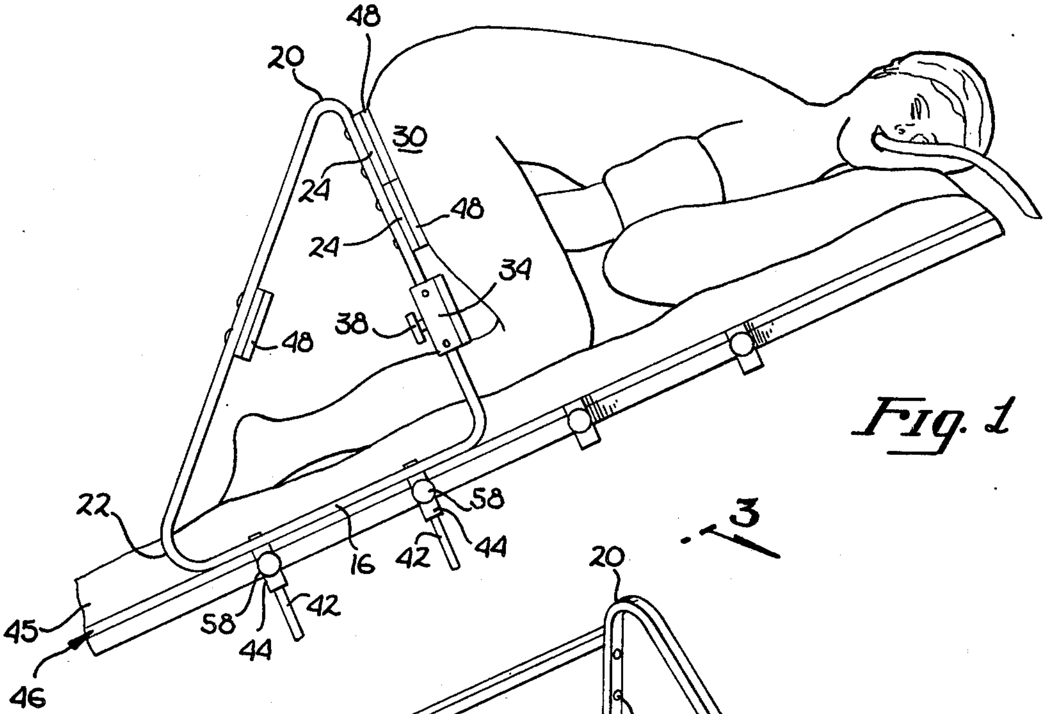
FIG. 1 is an illustration of the inverted support frame affixed to an operating table, with a patient placed in proper position thereon.
Figure 2:
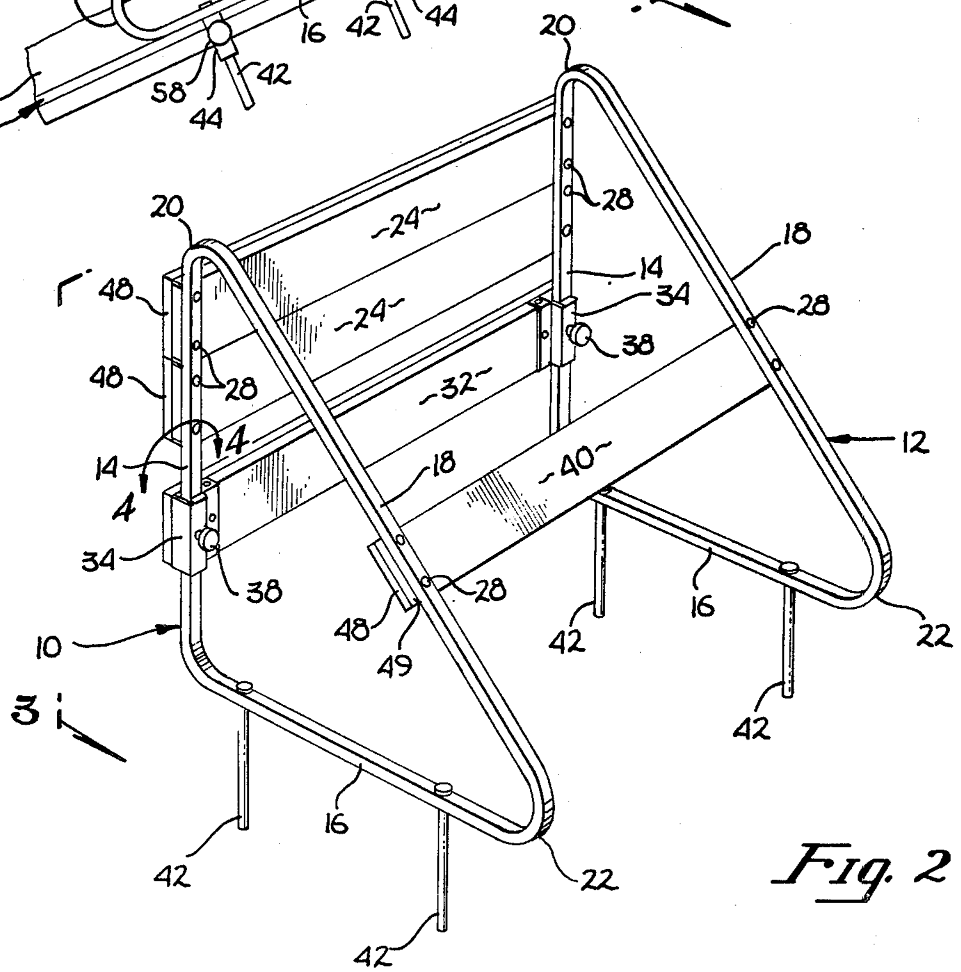
FIG. 2 is a perspective view of the present invention.

Referring first to FIGS. 1 and 2, the orthopedic support frame of the present invention is shown comprising two brackets 10 and 12, each having a first member 14, a second member 16 and a third member 18. Members 14 and 16 are at substantially right angles to each other. Third members 18 extend from one end 20 of first members 14 to one end 22 of second member 16 such that brackets 10 and 12 are triangular shaped. In the preferred embodiment, the ends 20 and 22 are arcuate so that there are no sharp or pointed edges that may harm the patient once he is placed on the orthopedic support frame.

Extending across brackets 10 and 12 are a plurality of posterior support members 24. In the preferred embodiment, there are two support members 24 which together are wide enough to accommodate the posterior of even a very large size patient. The inventor has found that the most desirable dimensions for each support manager are as follows: $25\frac{1}{2}''$ long by $4\frac{1}{4}''$ wide. Support members 24 are rigidly mounted to brackets 10 and 12 by a plurality of bolts 28 extending through brackets 10 and 12 into support members 24. However, any rigid affixing means may be used. Posterior support members 24 are utilized to support the patient's buttocks 30 as shown in FIG. 1.

Figure 3:
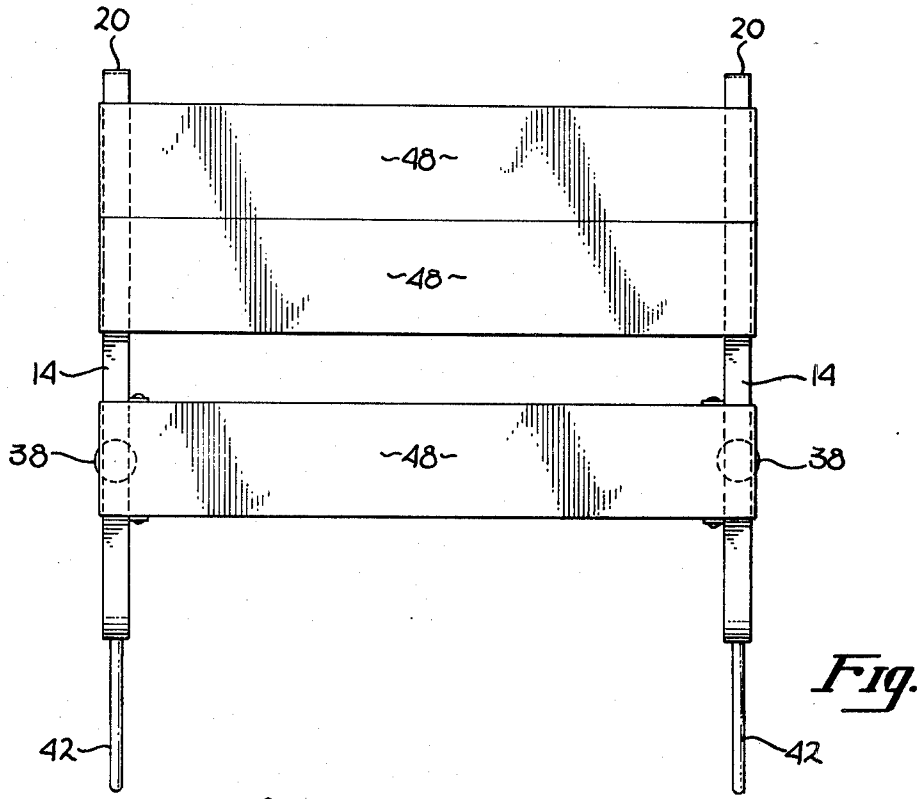
FIG. 3 is a front view of the present invention taken along lines 3—3 of FIG. 2.
Figure 4:
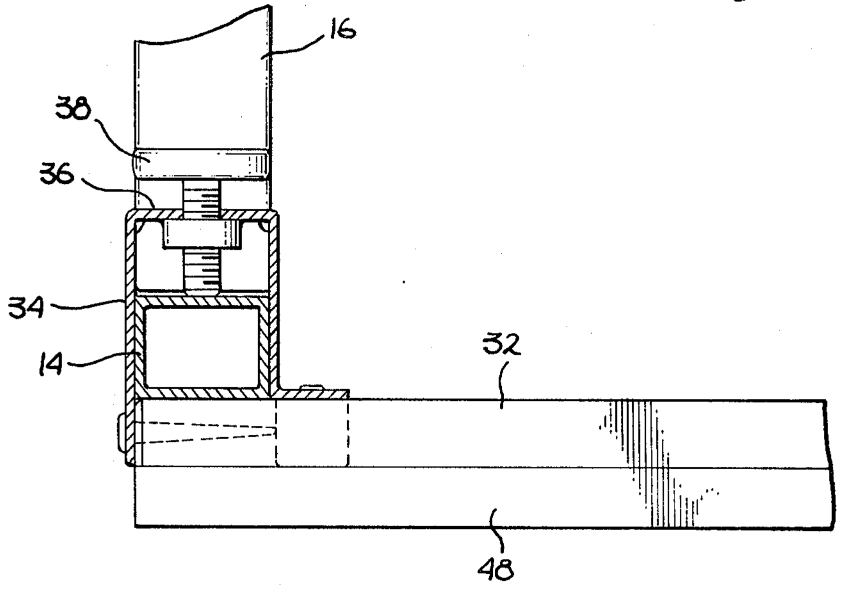
FIG. 4 is a cross sectional view of a portion of the locking member taken along lines 4—4 of FIG. 2.

Also extending across brackets 10 and 12 is an adjustable locking member 32 which is also seen in FIGS. 3 and 4. Locking member 32 has clamps 34 riveted on each end thereof for fixing member 32 on first members 14 of the brackets. Clamps 34 slidably surround first members 14. However any movable means capable of being repeatedly affixed in a locked position can be used in lieu of clamps 34. Clamps 34 comprise knurled knobs 38 which are attached to screws 37 which extend toward first members 14 such that when knob 38 is turned clockwise clamps 34 tightly affix locking members 32 to first members 14 in the desired position on the brackets 10 and 12.

Positioned across third frame members 18 is a cross member 40 fixedly mounted thereto to provide additional structural strength to the frame. For example, cross member 40 aids in preventing separation of the brackets 10 and 12 when the weight is excessive and aids in keeping the brackets 10 and 12 aligned so that the frame can be used with any standard operating table. Cross member 40 is affixed to brackets 10 and 12 through the use of bolts 28 extending through third frame members 18 into cross member 40.

Support members 24, locking member 32 and cross member 40 are made interchangeable for ease of assembly. Each comprises a beam 49 comprised of 440 stainless steel. However, non-rust aluminum, anodized aluminum or any sturdy rust-proof metal may be used. On the outer surface of each member is a protective coating 48 formed of FDA approved medical grade closed cell foam, although any gas-sterilizable, waterproof, bacteria resistant, non-toxic padding may be used. The foam 48 protects the patient from the cool temperatures of the steel beams and from any rough edges or exposed bolts 28.

Another advantage obtained by making members 24, 32, and 40 interchangeable is that, if member 24 becomes malfunctional (e.g. the foam breaks down, etc.), a cross member or locking member can be substituted in its place.

In order to affix the frame to an operating table 45 having side rails 46, a plurality of mounting rods 42 extend from the bottom of second frame members 16. In the preferred embodiment, mounting rods 42 are bolts which are affixed to the second frame members by nuts 43. Affixed to the rails 46 of the operating table are a plurality of rail clamps 44 into which the mounting rods may be inserted. By adjusting the depth that the mounting rods are inserted in the rail clamps 44, the height that the frame is disposed over the table may be adjusted. As a result, patients who are much larger than usual may be accommodated with the same frame. Further, the frame may be placed over any location on the table by inserting the mounting rods in any of the plurality of rail clamps 44.

To use the invention during surgery, the patient is placed face down on the operating table. The frame is placed over the patient on the operating table, until it is positioned directly over the back of the patient's legs. At this time mounting rods 42 are inserted into the appropriate rail clamps 44 on side rails 46 and knobs 48 on the rail clamps are tightened to immobilize the frame in position so that posterior support members 24 are as far from the surface of the table as the length of the distance between the buttocks and knees of the patient. Locking member 32 is then slid down first frame members 14 of the support brackets 10 and 12 until it rests against the legs just below the back of the patient's knees. Then, knobs 38 are tightened to immobilize the locking member 32 so that the patient will be unable to move during rotation of the operating table and during surgery. The operating table is then rotated to a reverse Trendelenberg position, approximately a 45° angle, such that the patient's body is pulled down into a sitting position whereby the patient's posterior and thighs are supported by posterior support members 24 as shown in FIG. 1. The patient is then in the modified knee-chest position for surgery.

Thus, an orthopedic frame has been described which places the patient in optimal modified knee-chest position for surgery. The frame facilitates exposure of the spinal interlaminar spaces, minimizes local hemorrhaging due to lack of pressure on the abdominal wall and also permits proper ventilation of the anesthetized patient by not compressing the chest, or abdomen.

While the invention has been disclosed and described with respect to a specific preferred embodiment thereof, it will be understood by those skilled in the art that various changes in form and detail may be made therein without departing from the spirit and scope of the invention.

What is claimed is:

1. An orthopedic support frame for supporting a patient prior to and during surgery on an operating table having side rails and rail clamps disposed along said side rails, said frame containing brackets, comprising:

(a) first and second bracket members each comprising first and second frame members, each affixed at substantially right angles to each other, and a third frame member affixed to said first second frame members so that each of said first and second bracket members has a substantially triangular shape, said first and second bracket members being parallel set apart in parallel relationship;

(b) at least one posterior support means extending at least from said first bracket member to said second bracket member and being rigidly affixed to the upper portion of said first and second bracket members for supporting the posterior of the patient, (c) locking member movably mounted upon said first frame members of said first and second brackets members below said posterior support means, said locking member being capable of being fixed at any position on said first members between said posterior support means and said second frame members, mounting means extending downward from said second frame members of said first and second bracket members for mounting the frame to the operating table, said mounting means being capable of being inserted through said rail clamps on said side rails, at preselected depths;

whereby said locking member may be locked in position against rear of the patient's knee joints to fix said patient to said table such that when the operating table is rotated in a reverse Trendelenberg position, the patient's body moves into and remains a sitting position on said posterior support means such that the patient is in the optimal knee-chest position for orthopedic surgery.

2. The frame of claim 1, wherein said posterior support means comprises a padding means for protecting the patient's body, said padding means being disposed upon the surface of said posterior support means which is intended to contact the patient's body.

3. The frame of claim 2, further comprising a cross member affixed to said third members of said first and second bracket members.

4. The frame of claim 3, wherein said posterior support means, said locking member and said cross member are identical in configuration whereby said cross member or said locking member may be substituted for said posterior support means in the event the padding means thereon is damaged.

5. The frame of claim 2 wherein said padding means comprises a gas sterilizable, waterproof, bacteria resistant, non-toxic foam padding.

6. The frame of claim 1, wherein said first and second bracket members, said posterior support means, and said locking member are comprised of a rust-proof metal.

7. In an orthopedic support frame used with an operating table having side rails having rail clamps during lumbar spine surgery on a patient, the frame having parallel first and second triangularly shaped brackets, each bracket having a first, second and third frame members, said frame further comprising a cross member extending across the third members thereof, the improvements comprising:

a fixedly mounted seating platform, accommodating any size, shape or weight patient, affixed across the first frame members of said first and second support brackets;

a locking member adjustably mounted across said first frame members of said first and second brackets below said seating platform, said locking member being capable of being affixed to any position on said first members between said seating platform and said second members, whereby said locking member may be positioned to rest against the rear of the legs of the patient just below the patient's knee joints, thereby immobilizing said patient to said table such that when the operating table is rotated in a reverse Trendelenberg position, the patient's body moves into a sitting position on said seating platform such that the patient is in and remains a knee-chest position for orthopedic surgery.

8. The frame of claim 7 further comprising covering means for covering said seating platform, said locking member and the cross member for protecting the patient from any rough edges on any element used as said seating platform.

9. The frame of claim 8, wherein said covering means comprises a gas sterilizable, waterproof, bacteria resistant, non-toxic foam padding.

10. The frame of claim 7 wherein the first and second brackets, said seating platform and said cross member are each comprised of rust-proof metal.

* * * * *